(12) United States Patent
Miyoshi et al.

(10) Patent No.: US 11,493,745 B2
(45) Date of Patent: Nov. 8, 2022

(54) CELL OBSERVATION SYSTEM

(71) Applicant: EVIDENT CORPORATION, Nagano (JP)

(72) Inventors: Takashi Miyoshi, Kanagawa (JP); Shinichi Takimoto, Tokyo (JP); Yasunobu Iga, Tokyo (JP); Shintaro Takahashi, Tokyo (JP)

(73) Assignee: Evident Corporation, Tokyo (JP)

( * ) Notice: Subject to any disclaimer, the term of this patent is extended or adjusted under 35 U.S.C. 154(b) by 354 days.

(21) Appl. No.: 16/724,372

(22) Filed: Dec. 22, 2019

(65) Prior Publication Data

US 2020/0124836 A1 Apr. 23, 2020

Related U.S. Application Data

(63) Continuation of application No. PCT/JP2017/023393, filed on Jun. 26, 2017.

(51) Int. Cl.
*G02B 21/36* (2006.01)
*G06T 7/00* (2017.01)
*C12M 1/00* (2006.01)

(52) U.S. Cl.
CPC ......... *G02B 21/361* (2013.01); *G02B 21/362* (2013.01); *G06T 7/0012* (2013.01); *C12M 41/14* (2013.01)

(58) Field of Classification Search
CPC .. G02B 21/361; G02B 21/362; G06T 7/0012; C12M 41/14
See application file for complete search history.

(56) References Cited

U.S. PATENT DOCUMENTS 4,907,158 A 3/1990 Kettler et al.
2003/0081209 A1 5/2003 Takahashi et al.
(Continued)

FOREIGN PATENT DOCUMENTS

CN 103582697 A 2/2014
EP 2719754 A1 4/2014
(Continued)

OTHER PUBLICATIONS

Office Action (Non-Final Rejection) dated Dec. 13, 2021, issued in related U.S. Appl. No. 16/724,375.
(Continued)

*Primary Examiner* — Jae N Noh
(74) *Attorney, Agent, or Firm* — Holtz, Holtz & Volek PC

(57) ABSTRACT

A cell observation system according to the present invention includes: a first image-acquisition device disposed in an incubator and acquires a first image of cells in a culturing vessel; a second image-acquisition device disposed outside the incubator; a processing device connected to the first image-acquisition device and the second image-acquisition device; and a display displays at least a region of the first image, as well as the second image. The second image-acquisition device includes a second image-acquisition unit that acquires a second image of the interior of the culturing vessel, that removed from the incubator. The processing device extracts target cells in the first image, calculates positions at which the extracted target cells are present and stores the positions in the memory, and causes the display to display the positions at which the target cells are present in a superimposed manner on an indication indicating the culturing vessel.

8 Claims, 6 Drawing Sheets

(56) References Cited

U.S. PATENT DOCUMENTS

| | | | |
|---|---|---|---|
| 2003/0103662 | A1 | 6/2003 | Finkbeiner |
| 2004/0152188 | A1 | 8/2004 | Yamamoto et al. |
| 2006/0115892 | A1 | 6/2006 | Yamamoto et al. |
| 2011/0013821 | A1* | 1/2011 | Mimura ............... G06T 7/0016 382/133 |
| 2013/0027539 | A1 | 1/2013 | Kiyota et al. |
| 2013/0309710 | A1 | 11/2013 | Nakamura |
| 2014/0092228 | A1 | 4/2014 | Usuba et al. |
| 2014/0327758 | A1* | 11/2014 | Hsiung ............... G02B 21/365 348/79 |
| 2019/0339498 | A1 | 11/2019 | Matsubara |
| 2020/0110922 | A1 | 4/2020 | Shinoda |
| 2020/0126225 | A1* | 4/2020 | Miyoshi ............... G06T 7/254 |

FOREIGN PATENT DOCUMENTS

| | | |
|---|---|---|
| JP | S643560 A | 1/1989 |
| JP | H08338705 A | 12/1996 |
| JP | 2001025387 A | 1/2001 |
| JP | 2003130866 A | 5/2003 |
| JP | 2004180675 A | 7/2004 |
| JP | 2005514589 A | 5/2005 |
| JP | 2005265717 A | 9/2005 |
| JP | 2005348688 A | 12/2005 |
| JP | 2009106305 A | 5/2009 |
| JP | 2009282198 A | 12/2009 |
| JP | 2010112969 A | 5/2010 |
| JP | 2011022322 A | 2/2011 |
| JP | 2011196867 A | 10/2011 |
| JP | 2015231343 A | 12/2015 |
| NO | 2003048705 A1 | 6/2003 |
| WO | 2011089908 A1 | 7/2011 |
| WO | 2013094365 A1 | 6/2013 |
| WO | 2015107667 A1 | 7/2015 |
| WO | 2019003271 A1 | 1/2019 |

OTHER PUBLICATIONS

Notice of Termination of Reconsideration by Examiners before Appeal Proceedings (and English language translation thereof) dated Feb. 2, 2022, issued in Japanese Application No. 2019-526406 (which is a Japanese counterpart of related U.S. Appl. No. 16/724,375).

Reconsideration Report by Examiner before Appeal (and English language translation thereof) dated Jan. 25, 2022, issued in Japanese Application No. 2019-526406 (which is a Japanese counterpart of related U.S. Appl. No. 16/724,375).

International Search Report (ISR) dated Sep. 26, 2017 (and English translation thereof), issued in International Application No. PCT/JP2017/023393.

International Search Report (ISR) dated Sep. 5, 2017 (and English translation thereof), issued in International Application No. PCT/JP2017/023388.

Written Opinion of the International Searching Authority dated Sep. 26, 2017 issued in International Application No. PCT/JP2017/023393.

Written Opinion of the International Searching Authority dated Sep. 5, 2017 issued in International Application No. PCT/JP2017/023388.

Japanese Office Action (and English language translation thereof) dated Jun. 22, 2021 issued in Japanese Application No. 2019-526406.

Related U.S. Appl. No. 16/724,375, First Named Inventor: Takashi Miyoshi; Title: "Cell Observation System"; filed Dec. 22, 2019.

* cited by examiner

CELL OBSERVATION SYSTEM

CROSS-REFERENCE TO RELATED APPLICATIONS

This is a continuation of International Application PCT/JP2017/023393, with an international filing date of Jun. 26, 2017, which is hereby incorporated by reference herein in its entirety.

TECHNICAL FIELD

The present invention relates to a cell observation system.

BACKGROUND ART

There is a known technology for collecting and removing target cells from a culturing vessel while observing the interior of the culturing vessel by using an observation device in a workspace such as a clean bench (for example, see Japanese Unexamined Patent Application, Publication No. 2009-106305).

SUMMARY OF INVENTION

An aspect of the present invention is a cell observation system including: a first image-acquisition device that is disposed in an incubator, the first image-acquisition device is provided with a first image-acquisition unit that acquires a first image of cells in a culturing vessel; a second image-acquisition device that is disposed outside the incubator, the second image-acquisition device is provided with a second image-acquisition unit that acquires a second image of the interior of the culturing vessel, which has been removed from the incubator; a processing device that is connected to the first image-acquisition device and the second image-acquisition device; and a display that is connected to the processing device and that displays at least a region of the first image, as well as the second image being acquired by the second image-acquisition unit. The processing device extracts target cells in the first image acquired by the first image-acquisition device, calculates positions at which the extracted target cells are present and stores the positions in the memory, and causes the display to display the positions at which the target cells are present in a superimposed manner on an indication indicating the culturing vessel.

DESCRIPTION OF EMBODIMENT

A cell observation system 1 according to an embodiment of the present invention will be described below with reference to the drawings.

Figure 1:
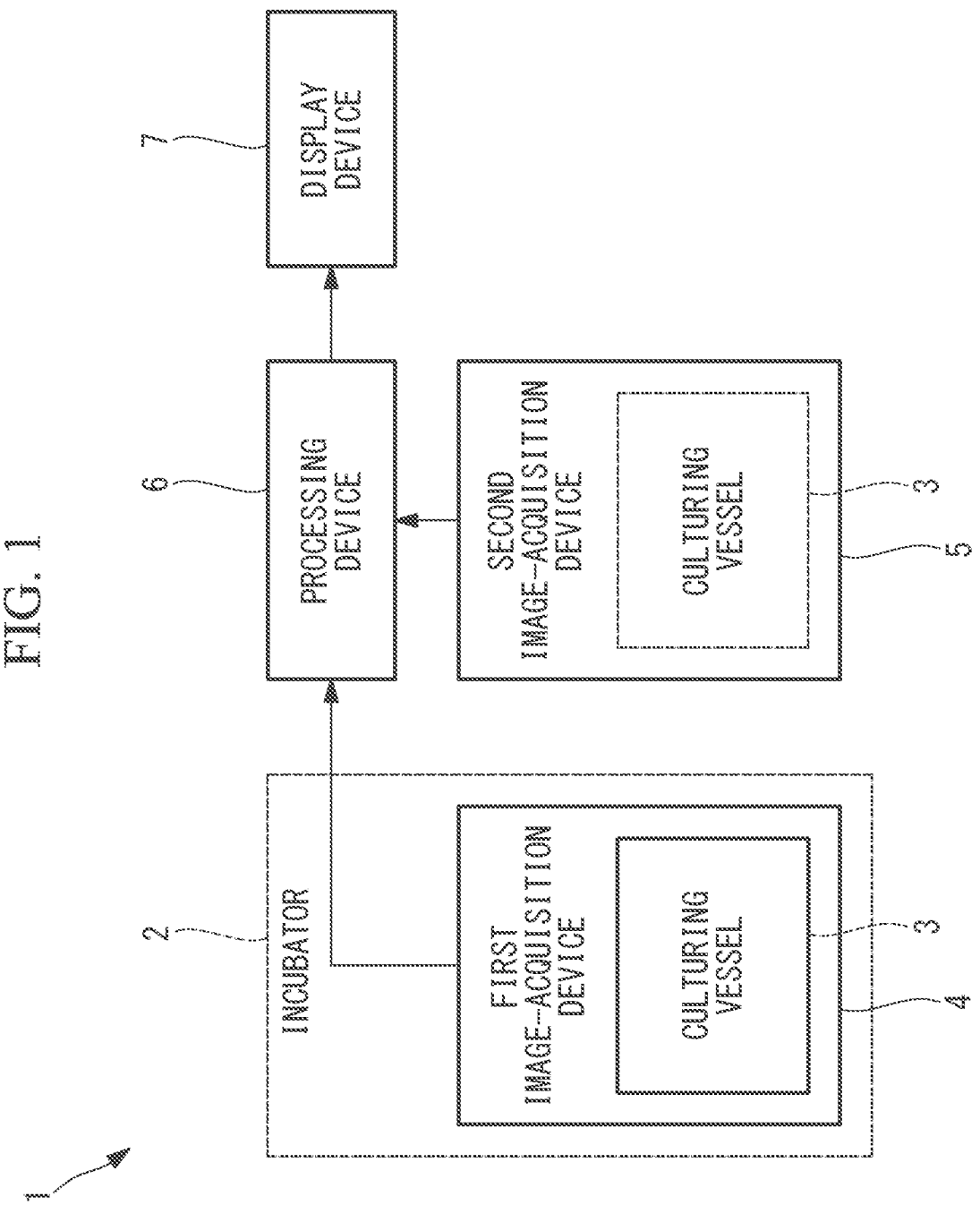
FIG. 1 is a block diagram showing a cell observation system according to an embodiment of the present invention.

As shown in FIG. 1, the cell observation system 1 according to this embodiment includes: a first image-acquisition device 4 that is disposed in an incubator 2 for culturing cells (see FIG. 5) X, that has a culturing vessel 3 seeded with the cells X placed thereon, and that acquires a first image of the cells X in the culturing vessel 3; a second image-acquisition device 5 that is disposed outside the incubator 2, that has the culturing vessel 3 that has been removed from the incubator 2 placed thereon, and that acquires a second image of the cells X in the culturing vessel 3; a processing device 6 that is connected to the first image-acquisition device 4 and the second image-acquisition device 5; and a display 7 that is connected to the processing device 6.

Figure 2:
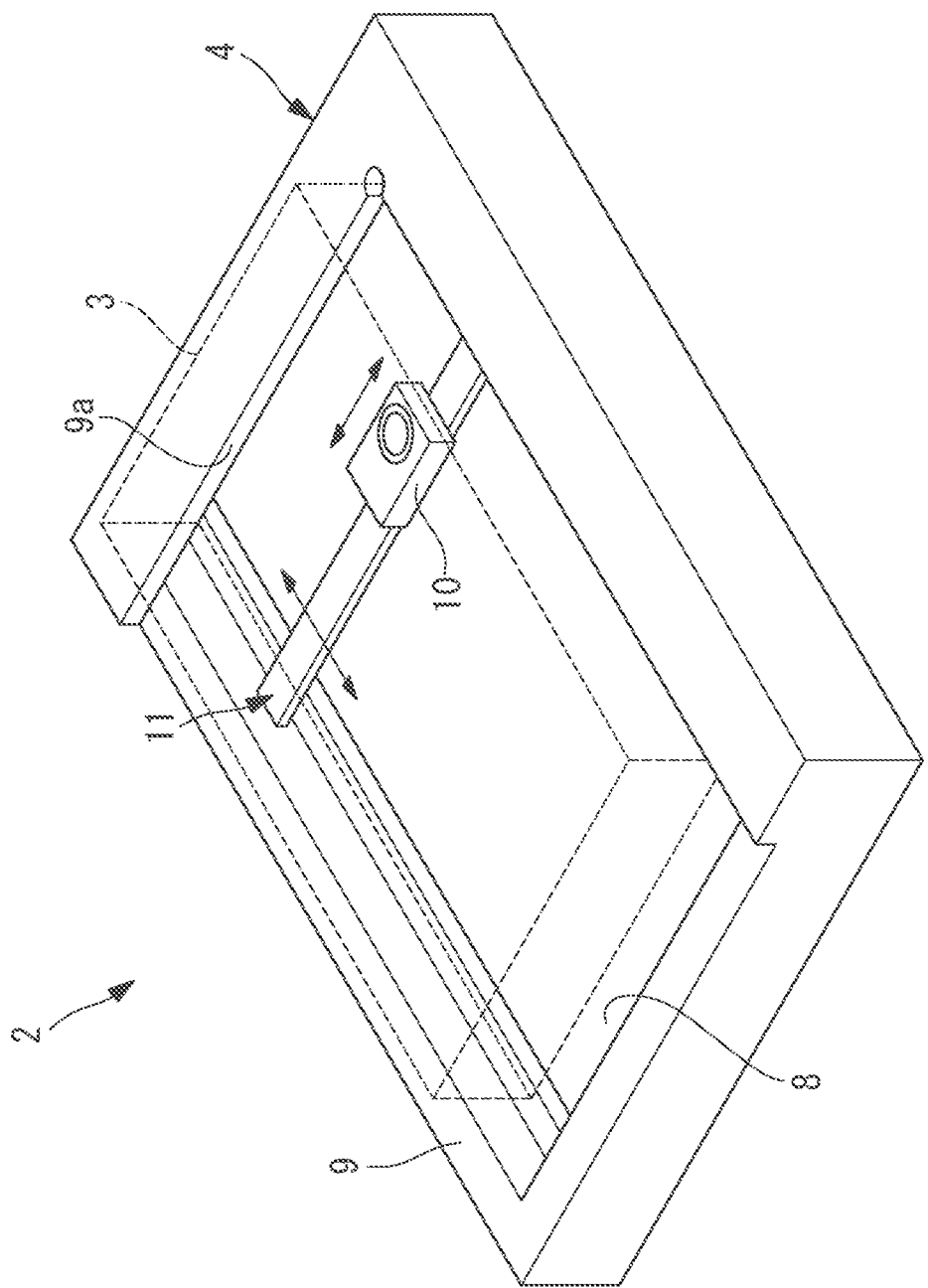
FIG. 2 is a plan view showing a first image-acquisition device provided in the cell observation system in FIG. 1.

As shown in FIG. 2, the first image-acquisition device 4 includes: a stage 9 on which the culturing vessel 3 having at least a bottom surface made of an optically transparent material is placed, and that has a window 8 that is at least partially transparent; a first image-acquisition unit 10 that captures images of the cells X in the culturing vessel 3 placed on the stage 9 from below the stage 9; and a driving unit 11 that moves the first image-acquisition unit 10 in two horizontal directions with respect to the stage 9.

The culturing vessel 3 is, for example, a multiwell plate that has a rectangular external shape and that has six circular wells arranged in two rows and three columns. The wells are seeded with the cells X and filled with a culturing liquid.

The stage 9 includes two abutting surfaces 9a against which two adjacent side surfaces of the culturing vessel 3 placed on the stage 9 are abutted, and, as a result of individually abutting the two side surfaces of the culturing vessel 3 against the two abutting surfaces 9a, it is possible to place the culturing vessel 3 in a positioned state.

The first image-acquisition unit 10 is a camera that includes a required optical system such as a focusing lens, and is provided with a field of view that is sufficiently smaller than the bottom surface of the culturing vessel 3.

The driving unit 11 includes, for example: a motor; a slider on which the first image-acquisition unit 10 is placed; and two linear motion mechanisms that convert the motive power of the motor into the motions of the slider in two horizontal directions, although these components are not illustrated. The motor includes an encoder (not shown), and thus, it is possible to detect the position (relative position) of the first image-acquisition unit 10 in the horizontal direction when the driving unit 11 is operated, assuming that the first image-acquisition unit 10 is at the origin in the state in which the optical axis of the first image-acquisition unit 10 is disposed at a prescribed position with respect to the intersection of the two abutting surfaces 9a.

By doing so, the first image-acquisition device 4 transmits, to the processing device 6, the images (partial images) acquired by the first image-acquisition unit 10 as a result of moving the first image-acquisition unit 10 to the prescribed position by causing the driving unit 11 to be driven and the position of the first image-acquisition unit 10 detected by the encoder at that time, in association with each other.

Figure 3:
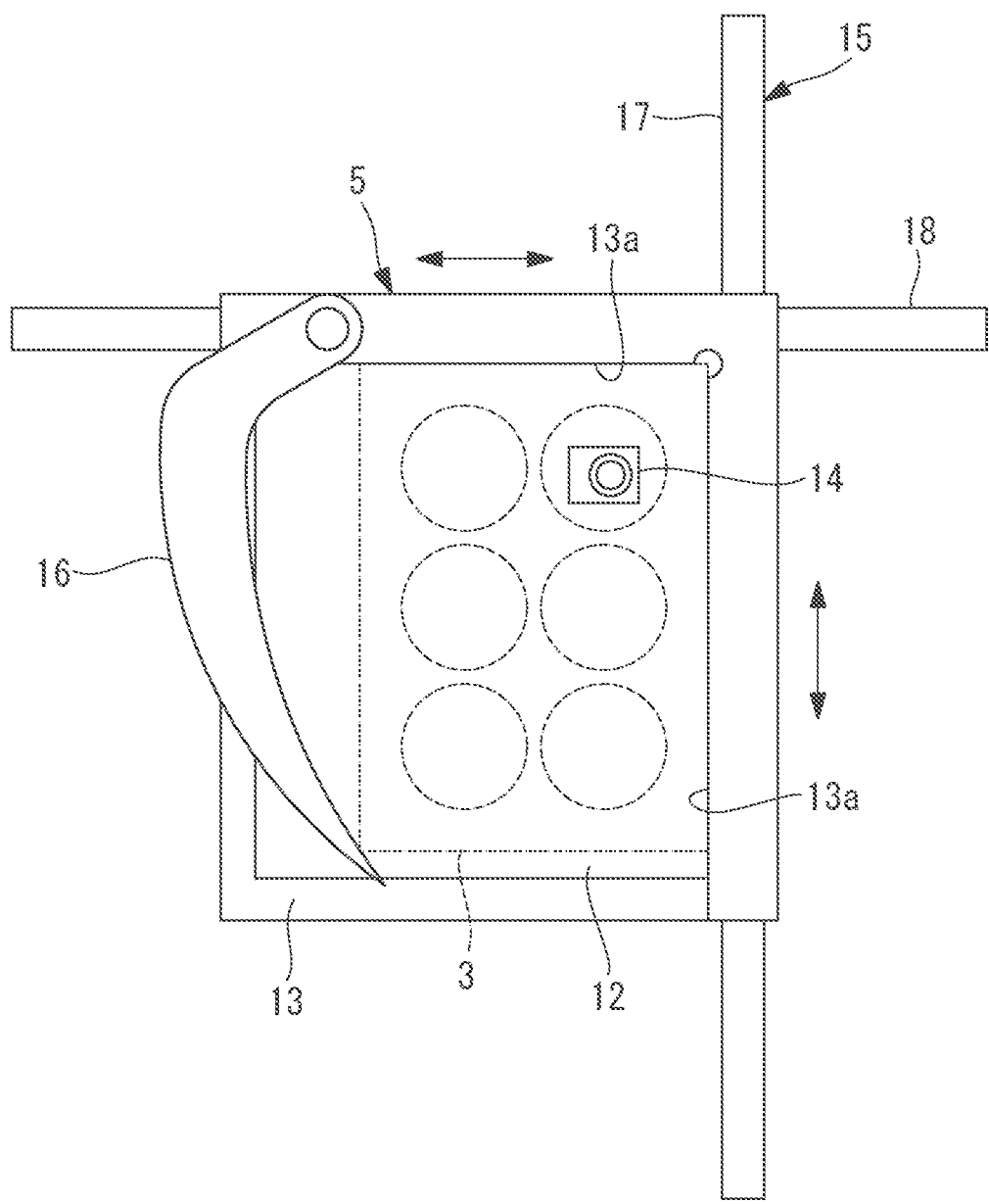
FIG. 3 is a plan view showing a second image-acquisition device provided in the cell observation system in FIG. 1.

As shown in FIG. 3, the second image-acquisition device 5 includes: a slide stage 13 that has a window 12 that is at least partially transparent; a second image-acquisition unit 14 that is disposed below the slide stage 13 and that captures images of the cells X in the culturing vessel 3 placed on the slide stage 13; and a support 15 that supports the slide stage 13 so as to be movable in two horizontal directions.

The second image-acquisition unit 14 is a camera that includes a required optical system such as a focusing lens, and has a magnification that is lower than that of the first image-acquisition unit 10 or a magnification that is equivalent to that of the first image-acquisition unit 10. The second image-acquisition unit 14 may be configured so that it is possible to switch to a higher magnification for performing a detailed check.

The slide stage 13 includes: two abutting surfaces 13*a* against which two adjacent side surfaces of the culturing vessel 3 placed on the slide stage 13 are abutted; and a vessel clamp 16 that, as a result of sandwiching the culturing vessel 3 between the vessel clamp 16 and the two abutting surfaces 13*a*, secures the culturing vessel 3 to the slide stage 13 in a positioned state. The vessel clamp 16 is biased, by means of a spring (not shown), in a direction in which the distances between the vessel clamp 16 and the two abutting surfaces 13*a* are reduced.

The support 15 includes: guide rails 17 and 18 that guide the slide stage 13 in two directions that are orthogonal to each other.

The processing device 6 includes a processor and a memory that are not illustrated. By means of the processor, the processing device 6 receives the plurality of images transmitted from the first image-acquisition device 4 and the positions of the first image-acquisition unit 10 at the time of acquiring the respective images, generates a larger first image in which the plurality of images are combined, and processes the generated first image, thus extracting target cells.

It is possible to extract the target cells as cells differing from the other cells X, for example, by calculating shape features of the cells X. The processing device 6 stores, for example, the center-of-gravity positions of the extracted target cells in the memory as the positions of the target cells.

Figure 4:
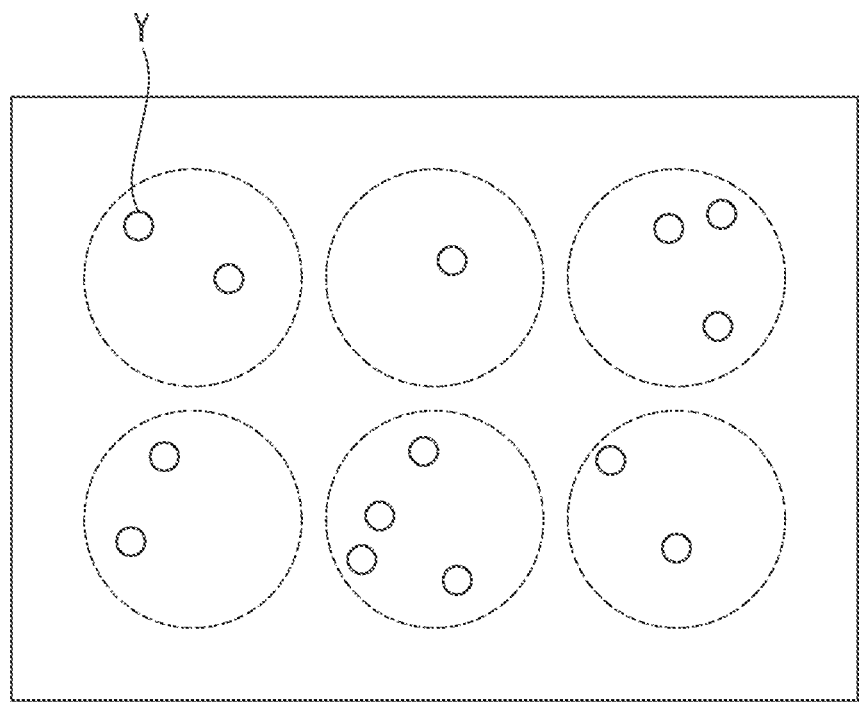
FIG. 4 is a diagram showing an example of a well guide to be displayed on a display of the cell observation system in FIG. 1.

Then, as shown in FIG. 4, after completing extraction of the target cells in all regions in the first image, the processing device 6 generates marks Y, which indicate positions at which the target cells are present, in a well guide superimposed on a vessel-dimension image representing the culturing vessel 3. A user can select any one of the marks Y displayed on the well guide, and once a mark Y is selected, the processing device 6 causes the display 7 to display a first image containing a target cell extracted at the position corresponding to the mark Y.

Figure 5:
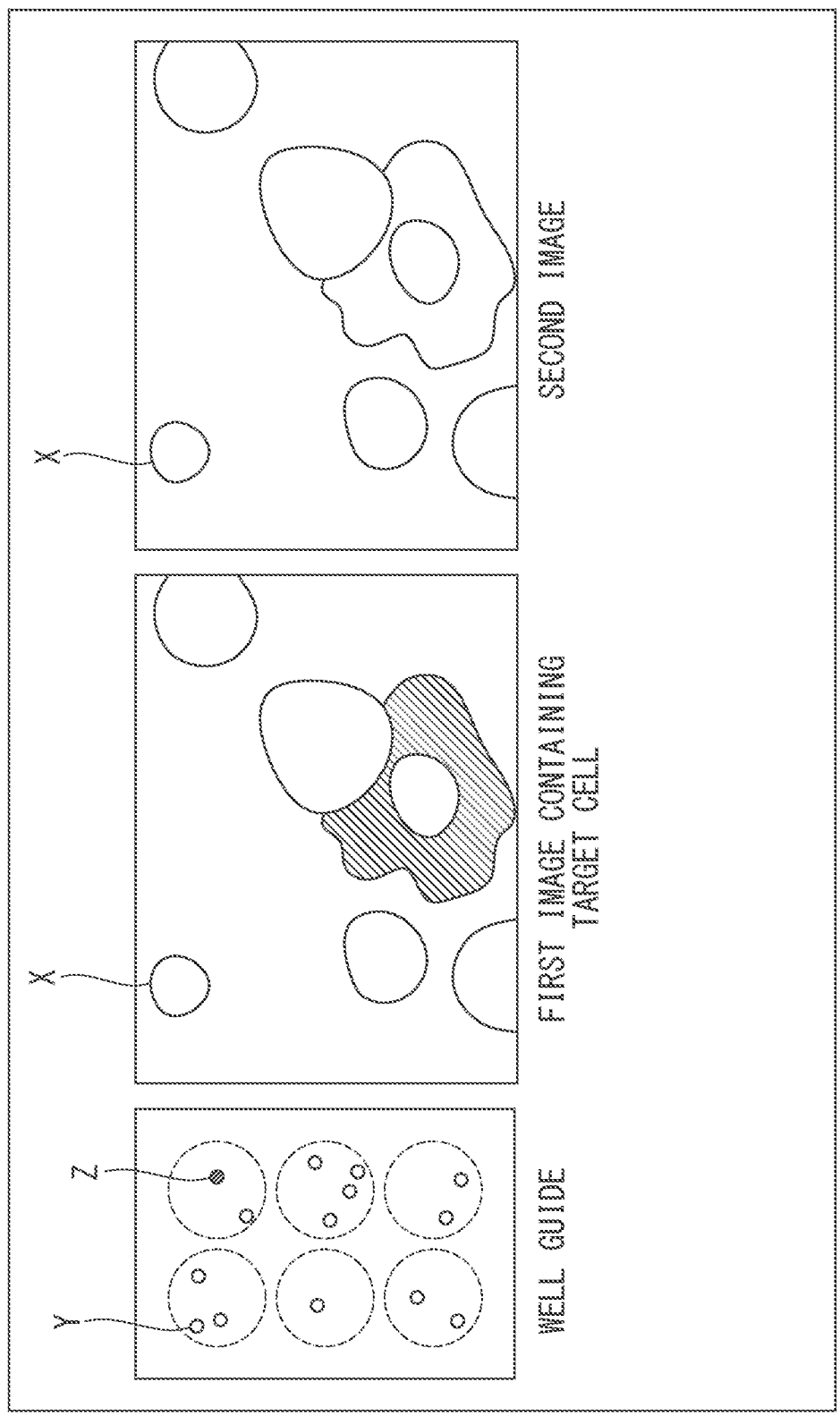
FIG. 5 is a diagram showing a display example on the display of the cell observation system in FIG. 1.

Therefore, as shown in FIG. 5, the processing device 6 causes the display 7 to display, next to each other, the well guide, the second image itself that is being currently acquired, and a region of the first image selected by the user. In the figure, the hatched region in the first image indicates a target cell.

Because the position in the culturing vessel 3 being captured by the second image-acquisition unit 14 changes when the user moves the culturing vessel 3 in the horizontal direction in the second image-acquisition device 5, the second image displayed on the display 7 changes in real time.

The operation of the cell observation system 1 according to this embodiment, thus configured, will be described below.

In order to observe the cells X by using the cell observation system 1 according to this embodiment, the culturing vessel 3 accommodating the cells X and a medium is placed on the stage 9 of the first image-acquisition device 4 in the incubator 2, and two adjacent side surfaces of the culturing vessel 3 are abutted against the two abutting surfaces 9*a* provided in the stage 9. By doing so, the culturing vessel 3 is placed on the stage 9 in a positioned state.

In this state, the cells X that grow adhering to the bottom surface of the culturing vessel 3 are cultured while the interior of the incubator 2 are managed so as to be at prescribed temperature and humidity. Then, for example, when the time for passaging the cells X is reached, the first image-acquisition device 4 is operated, a plurality of partial images of the cells X adhered to the bottom surface of the culturing vessel 3 are acquired, the positions of the optical axis of the first image-acquisition unit 10 at the time of acquiring the respective partial images are associated with the reference position of the stage 9, and this information is transmitted to the processing device 6 in association with the partial images.

The processing device 6 generates a first image having a greater angle of view by combining the plurality of partial images transmitted thereto, and performs processing in which target cells are extracted in the generated first image. Examples of the target cells include cells X determined to be cells that should be isolated or discarded by using a pipette or an aspirator as a result of distinguishing the colony states of the cells X.

As shown in FIG. 4, the processing device 6 generates a well guide that represents the shape of the culturing vessel 3, and superimposes, for example, circular marks Y at the positions extracted as being the target cells.

The user removes the culturing vessel 3 from the incubator 2, and places the culturing vessel 3 on the slide stage 13 of the second image-acquisition device 5 disposed in a clean bench outside the incubator 2. Then, the two side surfaces of the culturing vessel 3 are abutted against the two abutting surfaces 13*a* provided in the slide stage 13, and the culturing vessel 3 is secured on the slide stage 13 by means of the vessel clamp 16. By doing so, the well guide generated by the processing device 6 is displayed on the display 7, and the second image is acquired by the second image-acquisition unit 14 and is displayed on the display 7.

In response to the user selecting, on the well guide, a mark Y of a target cell he/she wants to be displayed, the processing device 6 causes the display 7 to display a first image containing the target cell at the position corresponding to the selected mark Y (in FIG. 5, the hatching on the well guide indicates that the mark Y is selected by the user). The user confirms the position of the selected mark Y in the culturing vessel 3 by using the well guide, and moves the slide stage 13 so that the second image-acquisition unit 14 is in a substantially equivalent positional relationship with respect to the culturing vessel 3.

By doing so, once the position of the second image-acquisition unit 14 is arranged so as to be at a position nearly aligned with the position of the selected mark Y with respect to the culturing vessel 3, as shown in FIG. 5, an image of the target cell appears in the second image being displayed on the display 7, and the first image and the second image are nearly aligned with each other. By doing so, it is possible to quickly identify, outside the incubator 2, the target cell extracted in the incubator 2. Therefore, the user can isolate the target cell by using a pipette or the like, and he/she can perform comparative observation between the first image before the isolation and the second image after the isolation.

As has been described above, with the cell observation system 1 according to this embodiment, the target cells are extracted by processing the first image acquired in the incubator 2, and the positions of the extracted target cells are displayed outside the incubator 2; therefore, the user can easily confirm the target cells by aligning the second image-acquisition unit 14 with the displayed positions, and he/she can quickly perform treatment such as isolation or the like.

Therefore, there is an advantage in that, as a result of reducing the time and effort for the user to search for the target cells, it is possible to find the target cells in the culturing vessel 3 in a comprehensive manner.

As a result, because it is not necessary to search for the target cells after removal from the incubator 2, it is possible to prevent the cells X from being exposed, for a long time, to a situation in which a culturing environment is not prepared, and thus, it is possible to maintain the cells X in a healthy state.

Note that, although the circular marks Y indicating the target cells are superimposed on the well guide indicating the culturing vessel 3 in this embodiment, in addition thereto, a region of the first image acquired by the first image-acquisition device 4 may be displayed in a superimposed manner. By doing so, the user can confirm the positions of the target cells while viewing the displayed first image, and thus, he/she can more intuitively confirm the target cells.

Although the vessel-dimension image is generated and displayed as the indication representing the culturing vessel 3, alternatively, the first image itself may be displayed.

Figure 6:
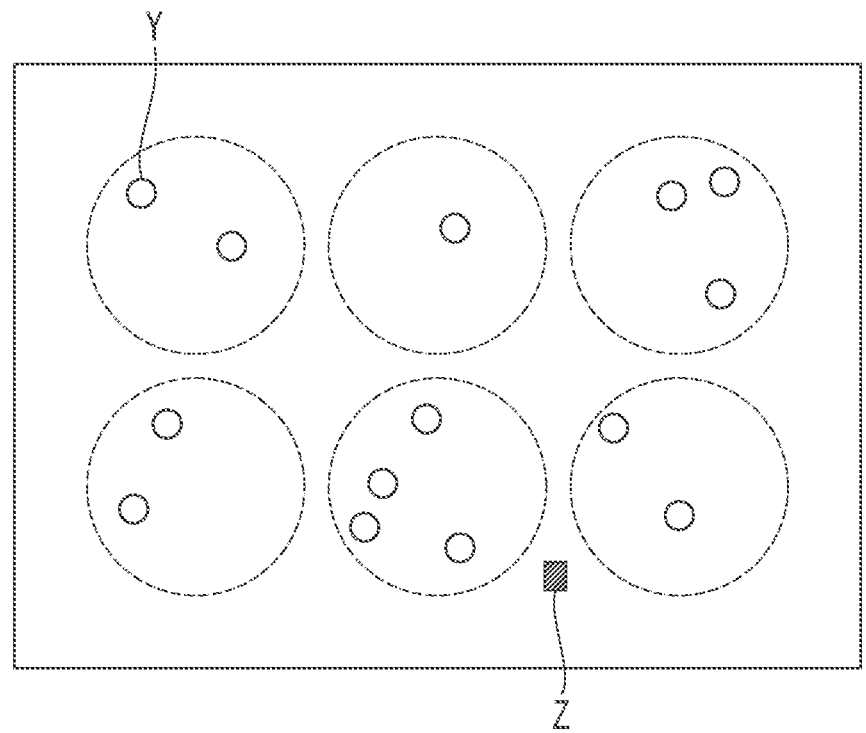
FIG. 6 is a diagram showing a modification in which a mark indicating the position of a second image-acquisition unit is superimposed on the well guide in FIG. 4.

In this embodiment, the position of the optical axis of the second image-acquisition unit 14 with respect to the culturing vessel 3 may be identified in the first image by searching for the second image acquired by the second image-acquisition unit 14 in the first image by performing image matching. Then, as shown in FIG. 6, the identified position of the second image-acquisition unit 14 may be displayed in a superimposed manner in the well guide, for example, by using a rectangular mark Z.

By doing so, it is possible to move the slide stage 13 so that the rectangular mark Z, which indicates the position of the optical axis of the second image-acquisition unit 14, approaches a mark Y, which is superimposed on the well guide and indicates the position of a target cell, and thus, it is possible to more quickly display the target cell in the second image.

In addition to displaying the rectangular mark Z, which indicates the position of the second image, in the well guide in a superimposed manner, a rectangular mark Z that represents the second image-acquisition unit 14 may be displayed in a superimposed manner. As a result of superimposing the rectangular mark Z representing the second image-acquisition unit 14 on the well guide, which represents the culturing vessel 3, it is possible to display the relationship between the culturing vessel 3 and the second image-acquisition unit 14 on the second image-acquisition device 5 in a manner that is closer to reality, and thus, the user can more intuitively operate the slide stage 13.

In this embodiment, the case in which the second image-acquisition device 5 includes the slide stage 13, the abutting surfaces 13a, and the vessel clamp 16 has been described as an example. As a result of fixing the orientation of the culturing vessel 3 when moving the culturing vessel 3, it is possible to facilitate image matching by aligning the orientation of a second image to be acquired with the orientation of the first image.

Figure 7:
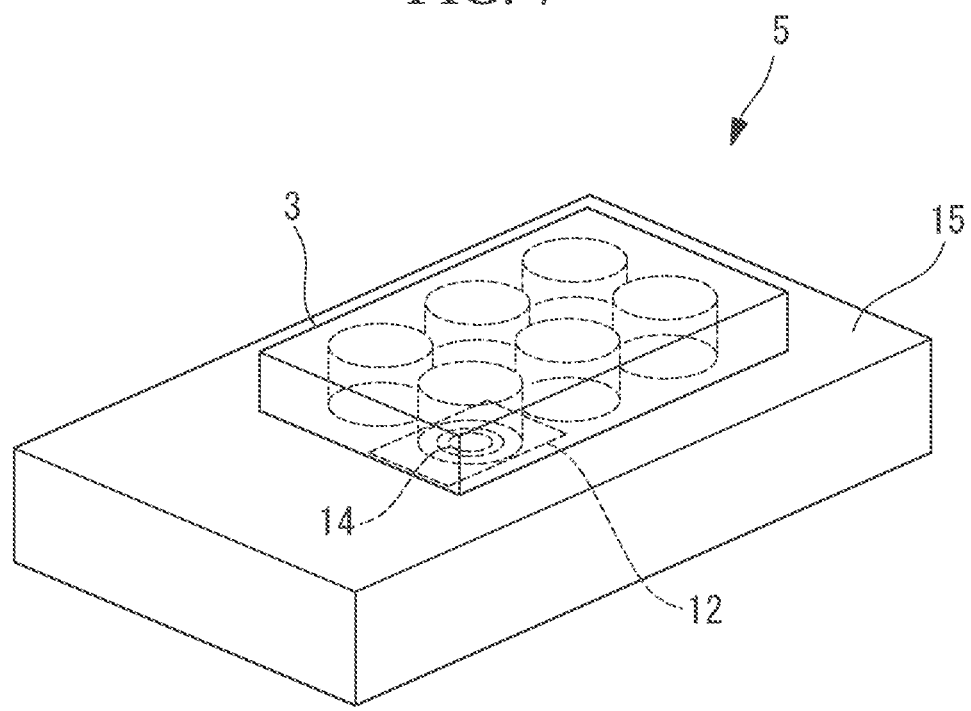
FIG. 7 is a perspective view showing a modification of the second image-acquisition device of the cell observation system in FIG. 1.

Alternatively, although image matching becomes complicated because it is necessary to take translation and rotation into account, as shown in FIG. 7, a transparent table-like stage that horizontally supports the culturing vessel 3 above the second image-acquisition unit 14 may be employed. By doing so, it is possible to acquire the second image by using the second image-acquisition unit 14 at arbitrary position and angle by freely sliding the culturing vessel 3 on the stage.

As a result, the following aspect is read from the above described embodiment of the present invention.

An aspect of the present invention is a cell observation system including: a first image-acquisition device that is disposed in an incubator, the first image-acquisition device is provided with a first image-acquisition unit that acquires a first image of cells in a culturing vessel; a second image-acquisition device that is disposed outside the incubator, the second image-acquisition device is provided with a second image-acquisition unit that acquires a second image of the interior of the culturing vessel, which has been removed from the incubator; a processing device that is connected to the first image-acquisition device and the second image-acquisition device; and a display that is connected to the processing device and that displays at least a region of the first image, as well as the second image being acquired by the second image-acquisition unit. The processing device extracts target cells in the first image acquired by the first image-acquisition device, calculates positions at which the extracted target cells are present and stores the positions in the memory, and causes the display to display the positions at which the target cells are present in a superimposed manner on an indication indicating the culturing vessel.

With this aspect, when the culturing vessel seeded with the cells is accommodated in the first image-acquisition device disposed in the incubator and the first image of the cells in the culturing vessel is acquired by the first image-acquisition unit, the acquired first image is transmitted to the processing device, the target cells in the first image are extracted, and the positions at which the target cells are present are calculated and stored.

When the culturing vessel and the second image-acquisition unit are moved relative to each other after removing the culturing vessel from the incubator and placing the culturing vessel on the second image-acquisition device disposed outside the incubator, the second image is acquired by the second image-acquisition unit.

The acquired first image, the second image, and the indication indicating the culturing vessel are displayed on the display, and the stored positions at which the target cells are present are displayed in a superimposed manner on the indication indicating the culturing vessel.

While a user is viewing the positions at which the target cells are present, superimposed on the indication indicating the culturing vessel, a second image can be displayed on the display in the vicinity of the positions at which the target cells are present by moving the culturing vessel and the second image-acquisition unit relative to each other. Thus, by doing so, it is possible to find the target cells in a comprehensive, effective manner in a workspace such as a clean bench or the like.

In the above-described aspect, the second image-acquisition device may include a support that supports the second image-acquisition unit and the culturing vessel in a movable manner relative to each other.

In the above-described aspect, the processing device may search for the second image in the first image by means of image matching, may calculate the relative position between the culturing vessel and the second image-acquisition unit, and may cause, on the basis of the calculated relative position, the display to display the correspondence relationship between the positions at which the target cells are present and the position of the second image currently being acquired.

By doing so, the processing device acquires, by means of image matching, the correspondence relationship between the positions of the target cells extracted in the first image and the position of the second image that is currently being acquired, and causes the display to display the correspondence relationship. While the user is viewing the correspondence relationship displayed on the display, it is possible to display on the display the second image containing the target cells by aligning the field of view of the second image-acquisition unit with the positions at which the target cells are present by moving the culturing vessel and the second image-acquisition unit relative to each other. Thus, by doing so, it is possible to find the target cells in a comprehensive, effective manner in a workspace such as a clean bench or the like.

In the above-described aspect, the first image-acquisition unit may acquire a plurality of partial images that constitute the first image, and the first image-acquisition device may be provided with a driving unit that moves the first image-acquisition unit and the culturing vessel relative to each other, and may transmit, to the processing device, the individual partial images and the relative positions between the culturing vessel and the first image-acquisition unit at the time of acquiring the partial images in association with each other.

By doing so, the first image-acquisition unit acquires the plurality of partial images of the cells in the culturing vessel, and the storage unit stores the individual partial images in association with the relative positions between the culturing vessel and the first image-acquisition unit at the time of acquiring the respective partial images. By doing so, it is possible to generate the first image having a greater size than the field of view of the first image-acquisition unit.

The indication indicating the culturing vessel may be a vessel-dimension image indicating the shape of the culturing vessel.

By doing so, it is possible to select the positions at which the target cells that are displayed in a superimposed manner are present, while viewing the vessel-dimension image displayed on the display.

In the above-described aspect, the processing device may cause the second image to be displayed in a superimposed manner on the indication indicating the culturing vessel.

By doing so, it is possible to save the display space as compared with the case in which the indication indicating the culturing vessel and the second image are separately displayed.

In the above-described aspect, the indication indicating the culturing vessel may be the first image, and the processing device may cause the second image to be displayed in a superimposed manner at a position corresponding to the second image in the first image.

By doing so, it is possible to additionally save the display space by utilizing the first image as the indication indicating the culturing vessel.

In the above-described aspect, the processing device may cause the first image acquired by the first image-acquisition device to be displayed at the positions at which the target cells are present.

By doing so, it is possible to quickly place the target cells in the second image by directly comparing the second image with the first image displayed at the positions at which the target cells are present.

REFERENCE SIGNS LIST 1 cell observation system
2 incubator
3 culturing vessel
4 first image-acquisition device
5 second image-acquisition device
6 processing device
7 display
10 first image-acquisition unit
11 driving unit
14 second image-acquisition unit
15 support
X cell

The invention claimed is:

1. A cell observation system comprising:
    a first image-acquisition device that is disposed in an incubator,
        the first image-acquisition device comprising
            a first image-acquisition unit that is configured to acquire a first image of cells in a culturing vessel;
    a second image-acquisition device that is disposed outside the incubator,
        the second image-acquisition device comprising
            a second image-acquisition unit that is configured to acquire a second image of an interior of the culturing vessel, which has been removed from the incubator;
    a processing device that is connected to the first image-acquisition device and the second image-acquisition device; and
    a display that is connected to the processing device and that is configured to display at least a region of the first image, as well as the second image acquired by the second image-acquisition unit,
    wherein: the processing device comprises at least one processor and a memory, and
    the at least one processor is configured to:
        extract target cells in the first image acquired by the first image-acquisition device,
        calculate positions at which the extracted target cells are present, and store the positions in the memory, and
        cause the display to display the positions at which the target cells are present in a superimposed manner on an indication indicating the culturing vessel.

2. The cell observation system according to claim 1, wherein the second image-acquisition device comprises a support that is configured to support the second image-acquisition unit and the culturing vessel so as to be movable relative to each other.

3. The cell observation system according to claim 1, wherein
    the at least one processor is configured to:
        search for the second image in the first image by performing image matching, and calculate a relative position between the culturing vessel and the second image-acquisition unit, and
        cause, based on the calculated relative position, the display to display a correspondence relationship between the positions at which the target cells are present and a position of the second image currently being acquired.

4. The cell observation system according to claim 1,
    wherein: the first image includes a plurality of partial images,
    the first image-acquisition unit acquires the partial images,
    the first image-acquisition device comprises a driving unit that is configured to move the first image-acquisition unit and the culturing vessel relative to each other, and the first image-acquisition device transmits, to the processing device, the individual partial images and relative positions between the culturing vessel and the first image-acquisition unit at a time of acquiring the partial images, in association with each other.

5. The cell observation system according to claim 1, wherein the indication indicating the culturing vessel is a vessel-dimension image indicating a shape of the culturing vessel.

6. The cell observation system according to claim 3, wherein the at least one processor is configured to cause the display to display the second image in a superimposed manner on the indication indicating the culturing vessel.

7. The cell observation system according to claim 3,
wherein: the indication indicating the culturing vessel is the first image, and
the at least one processor is configured to cause the display to display the second image in a superimposed manner at a position corresponding to the second image in the first image.

8. The cell observation system according to claim 1, wherein the at least one processor is configured to cause the display to display the first image acquired by the first image-acquisition device at the positions at which the target cells are present.

* * * * *

UNITED STATES PATENT AND TRADEMARK OFFICE
CERTIFICATE OF CORRECTION

PATENT NO. : 11,493,745 B2
APPLICATION NO. : 16/724372
DATED : November 8, 2022
INVENTOR(S) : Takashi Miyoshi et al.

It is certified that error appears in the above-identified patent and that said Letters Patent is hereby corrected as shown below:

On the Title Page

In item (73) change "Tokyo (JP)." to --Tatsuno-machi (JP)--.

Signed and Sealed this
Sixth Day of February, 2024

Katherine Kelly Vidal
*Director of the United States Patent and Trademark Office*